(12) United States Patent
Avula et al.

(10) Patent No.: US 10,520,414 B2
(45) Date of Patent: Dec. 31, 2019

(54) CONDENSATION PARTICLE COUNTER FALSE COUNT PERFORMANCE

(71) Applicant: TSI Incorporated, Shoreview, MN (US)

(72) Inventors: Sreenath Avula, Arden Hills, MN (US); Richard Remiarz, Vadnais Heights, MN (US); George John Chancellor, Lindstrom, MN (US); Tyler Anderson, Roseville, MN (US); Daniel C. Bjorkquist, Maplewood, MN (US); Robert Caldow, Roseville, MN (US); Sean Morell, Saint Paul, MN (US); Frederick R. Quant, Shoreview, MN (US); Susanne V. Hering, Berkeley, CA (US); Gregory S. Lewis, Berkeley, CA (US)

(73) Assignee: TSI Incorporated, Shoreview, MN (US)

( * ) Notice: Subject to any disclaimer, the term of this patent is extended or adjusted under 35 U.S.C. 154(b) by 0 days.

(21) Appl. No.: 15/552,396

(22) PCT Filed: Feb. 23, 2016

(86) PCT No.: PCT/US2016/019083
§ 371 (c)(1),
(2) Date: Aug. 21, 2017

(87) PCT Pub. No.: WO2016/137962
PCT Pub. Date: Sep. 1, 2016

(65) Prior Publication Data
US 2018/0045636 A1  Feb. 15, 2018

Related U.S. Application Data (60) Provisional application No. 62/119,558, filed on Feb. 23, 2015.

(51) Int. Cl.
*G01N 15/06* (2006.01)

(52) U.S. Cl.
CPC ... *G01N 15/065* (2013.01); *G01N 2015/0693* (2013.01)

(58) Field of Classification Search
CPC ......... G01N 15/065; G01N 2015/0693; G01N 15/0205; B01D 47/05; G03F 7/70091;
(Continued)

(56) References Cited

U.S. PATENT DOCUMENTS 3,632,210 A * 1/1972 Rich .................... G01N 15/065
250/574
4,770,238 A * 9/1988 Owen ................ F28D 15/0233
122/366

(Continued)

FOREIGN PATENT DOCUMENTS

| CN | 2769849 | 4/2006 |
| CN | 102890045 | 1/2013 |

(Continued)

OTHER PUBLICATIONS

"International Application Serial No. PCT/US2016/019083, International Preliminary Report on Patentability dated Sep. 8, 2017," 8 pgs.
(Continued)

*Primary Examiner* — Mohamed K Amara
(74) *Attorney, Agent, or Firm* — Schwegman Lundberg & Woessner, P.A.

(57) ABSTRACT

Various embodiments include methods of reducing false-particle counts in a water-based condensation particle counter (CPC). One embodiment of a method includes delivering water into one or more wicks, sensing an excess volume of water delivered to the wicks, collecting the excess volume of water into a collection reservoir, and draining the excess
(Continued)

volume of water from the collection reservoir. Other methods and apparatuses are disclosed.

20 Claims, 7 Drawing Sheets

(58) Field of Classification Search
CPC ............. G03F 7/70108; G03F 7/70208; G03F 7/70466; G03F 7/70566; G05D 23/22; G05D 23/24; Y10T 137/0318
See application file for complete search history.

(56) References Cited

U.S. PATENT DOCUMENTS

| | | | |
|---|---|---|---|
| 5,118,959 A * | 6/1992 | Caldow | G01N 15/065 250/573 |
| 5,903,338 A | 5/1999 | Mavliev et al. | |
| 6,517,612 B1 * | 2/2003 | Crouch | B01D 33/067 95/277 |
| 6,567,157 B1 * | 5/2003 | Flagan | G01N 1/2247 356/335 |
| 6,875,247 B2 * | 4/2005 | TeGrotenhuis | B01B 1/005 165/60 |
| 7,223,364 B1 * | 5/2007 | Johnston | B01L 3/5023 422/502 |
| 7,656,510 B2 | 2/2010 | Roberts et al. | |
| 8,449,657 B2 * | 5/2013 | Son | B01D 5/0027 356/37 |
| 2004/0069460 A1 * | 4/2004 | Sasaki | F28D 15/0241 165/104.26 |
| 2005/0227370 A1 * | 10/2005 | Ramel | G01N 33/726 436/514 |
| 2006/0146327 A1 * | 7/2006 | Wang | G01N 15/0266 356/338 |
| 2008/0083274 A1 * | 4/2008 | Hering | G01N 15/065 73/170.19 |
| 2008/0137065 A1 * | 6/2008 | Oberreit | G01N 30/84 356/37 |
| 2008/0144003 A1 * | 6/2008 | Blackford | G01F 1/661 356/37 |
| 2008/0186489 A1 | 8/2008 | Ahn | |
| 2009/0009749 A1 | 1/2009 | Ahn | |
| 2009/0165651 A1 * | 7/2009 | Burgess | B01D 39/2044 95/284 |
| 2010/0021777 A1 * | 1/2010 | Gottesfeld | H01M 8/0289 429/429 |
| 2010/0222752 A1 * | 9/2010 | Collins, Jr. | A61M 11/005 604/296 |
| 2010/0263731 A1 | 10/2010 | Hopke et al. | |
| 2010/0312499 A1 * | 12/2010 | Blackford | G01F 1/661 702/45 |
| 2011/0056273 A1 * | 3/2011 | Gorbunov | G01N 15/065 73/28.01 |
| 2014/0033915 A1 * | 2/2014 | Hering | B01D 47/00 95/1 |
| 2015/0160105 A1 * | 6/2015 | Caldow | G01N 15/065 356/246 |
| 2015/0268140 A1 * | 9/2015 | Wang | G01N 15/0227 356/335 |
| 2017/0276589 A1 * | 9/2017 | Oberreit | G01N 15/065 |
| 2019/0154550 A1 * | 5/2019 | Wu | G01N 33/54306 |

FOREIGN PATENT DOCUMENTS

| | | |
|---|---|---|
| JP | H0938639 A | 2/1997 |
| JP | H0970427 A | 3/1997 |
| JP | 2000234996 A | 8/2000 |
| JP | 2001074644 A | 3/2001 |
| JP | 2006232650 A | 9/2006 |
| JP | 2009014727 A | 1/2009 |
| JP | 2013142625 A | 7/2013 |
| JP | 2013536444 A | 9/2013 |
| JP | 2018509637 A | 4/2018 |
| KR | 20090003021 A | 1/2009 |
| KR | 101146302 B1 | 5/2012 |
| KR | 1020170136513 | 12/2017 |
| WO | WO-2014055652 A2 | 4/2014 |
| WO | WO-2016137962 A1 | 9/2016 |

OTHER PUBLICATIONS

"International Application Serial No. PCT/US2016/019083, International Search Report dated Jul. 1, 2016", 3 pgs.
"International Application Serial No. PCT/US2016/019083, Written Opinion dated Jul. 1, 2016", 6 pgs.
"Chinese Application Serial No. 201680020624.7, Office Action dated Aug. 5, 2019", with English translation, 17 pages.
"Japanese Application Serial No. 2017-562961, Notification of Reasons for Rejection dated Nov. 21, 2019", w/ English Translation, 6 pgs.

* cited by examiner

SECTION A-A

FIG. 2B

SECTION B-B    FIG. 2C

CONDENSATION PARTICLE COUNTER FALSE COUNT PERFORMANCE

CLAIM OF PRIORITY

This Patent Application is a U.S. National Stage Filing under U.S.C. § 371 from International Application Serial Number PCT/US2016/019083, filed on Feb. 23, 2016, and published as WO 2016/137962 on Sep. 1, 2016, which Patent Application claims the benefit of priority to U.S. Provisional Patent Application Ser. No. 62/119,558, filed on Feb. 23, 2015, which applications are hereby incorporated by reference in their entireties.

BACKGROUND

Condensation Particle Counters (CPCs) have different mechanisms to drain the working fluid out of the growth tube or wick. Most contemporary CPCs rely on gravity to drain the working fluid. However, as volumetric sample flow rates increase, any working fluid that drains in to the flow path has a tendency to create bubbles which then grow in to large particles that gets detected by an optical sensor within the CPC. Since these counts are generated internally to the CPC and are not caused by actual particles from a monitored environment, the internally-generated counts are considered "false-particle counts" and will occur even when the particle counter is sampling clean HEPA-filtered air. Performance of a CPC is rated by the number of false counts over a specified time period. For example, a semiconductor clean room may require less than six false counts per hour. Consequently, in general, the lower the number of false counts, the better the instrument. The disclosed subject matter discloses techniques and designs to reduce or eliminate false-particle counts in a CPC.

DETAILED DESCRIPTION

The description that follows includes illustrative examples, devices, and apparatuses that embody the disclosed subject matter. In the following description, for purposes of explanation, numerous specific details are set forth in order to provide an understanding of various embodiments of the inventive subject matter. It will be evident, however, to those of ordinary skill in the art that various embodiments of the inventive subject matter may be practiced without these specific details. Further, well-known structures, materials, and techniques have not been shown in detail, so as not to obscure the various illustrated embodiments.

As used herein, the term "or" may be construed in an inclusive or exclusive sense. Additionally, although various exemplary embodiments discussed below focus on particular ways to reduce false-particle counts by eliminating empty water droplets or bubbles being counted as actual particles, other embodiments consider electronic filtering techniques. However, none of these techniques needs to be applied to reducing or eliminating particle counts as a single technique. Upon reading and understanding the disclosure provided herein, a person of ordinary skill in the art will readily understand that various combinations of the techniques and examples may all be applied serially or in various combinations. As an introduction to the subject, a few embodiments will be described briefly and generally in the following paragraphs, and then a more detailed description, with reference to the figures, will ensue.

Reported count rates in contemporaneous water-based condensation particle counters (CPCs) are generally not acceptable for clean room applications due to the false-particle count rate. Current clean room requirements (e.g., in the semiconductor industry) specify a stringent false count rate of less than six counts per hour. Various embodiments disclosed herein include techniques and designs that were developed specifically to reduce or eliminate false counts caused by water bubbles or empty water droplets (e.g., detected "particles" not containing an actual particle serving as a nucleation point). Although various embodiments are discussed separately, these separate embodiments are not intended to be considered as independent techniques or designs. As indicated above, each of the various portions may be inter-related and each may be used separately or in combination with other false-count particle reduction techniques discussed herein.

In the following detailed description, reference is made to the accompanying drawings that form a part of the false-particle reduction techniques and in which is shown, by way of illustration, specific embodiments. Other embodiments may be utilized and, for example, various thermodynamic, electrical, or physical changes may be made without departing from the scope of the present disclosure. The following detailed description is, therefore, is to be taken in an illustrative sense rather than in a limiting sense.

In general, a condensation particle counter (also known as a condensation nucleus counter) is used to detect particles in a monitored environment that are too small to scatter enough light to be detected by conventional detection techniques (e.g., light scattering of a laser beam in an optical particle counter). The small particles are grown to a larger size by condensation formed on the particle. That is, each particle serves as a nucleation point for the working fluid; a vapor, which is produced by the instrument's working fluid, is condensed onto the particles to make them larger. After achieving growth of the particle due to condensation of the working fluid vapor onto the particle, CPCs function similarly to optical particle counters in that the individual droplets then pass through the focal point (or line) of a laser beam, producing a flash of light in the form of scattered light. Each light flash is counted as one particle. The science of condensation particle counters, and the complexity of the instrumentation, lies with the technique to condense vapor onto the particles. When the vapor surrounding the particles reaches a specific degree of supersaturation, the vapor begins to condense on the particles. The magnitude of supersaturation determines the minimum detectable particle size of the CPC. Generally, the supersaturation profile within the instrument is tightly controlled.

While there are several methods which can be used to create condensational growth, the most widely used technique is a continuous, laminar flow method. Continuous flow laminar CPCs have more precise temperature control than other types of CPCs, and they have fewer particle losses than instruments that use turbulent (mixing) flow. In a laminar flow CPC, a sample is drawn continuously through a conditioner region which is saturated with vapor and the sample is brought to thermal equilibrium. Next, the sample is pulled into a region where condensation occurs. In contrast, in an alcohol-based (e.g., (isopropanol or butanol) CPC, the conditioner region is at a warm temperature, and the condensation region (saturator) is relatively cooler. Water has very high vapor diffusivity, so a laminar flow water-based CPC with a cool condensation region does not work thermodynamically. In a laminar flow water-based CPC, the conditioner region is cool, and the condensation region is relatively warmer.

Water-based CPCs have a clear set of advantages over alcohol-based CPCs. Water is non-toxic, environmentally friendly, and easy to procure. Water however, also has a few disadvantages. In general, the liquid purity is not as tightly controlled for water as for alcohols purchased from chemical supply houses. The impurities in the water may build up in the "wick" (described below), and eventually cause the wick material to become ineffective. To counteract this impurity effect, distilled or high-purity water is frequently utilized. Additionally, the wicks are often field replaceable by an end-user. In some environments where extremely low particle counts are expected to be present (e.g., a semiconductor-fabrication facility), the end-user may use water specifically prepared and packaged for use in normal-phase liquid chromatography (NPLC). NPLC water is ultra-pure water with a low ultra-violet (UV) absorbance, often filtered through, for example, a 0.2 micrometer (μm) filter, and packaged in solvent-rinsed amber glass bottles and sealed under an inert atmosphere such as nitrogen. The use of NPLC water can help to reduce or eliminate false-particle counts from contaminants (e.g., ions, particles or bacteria) that may ordinarily be present in the water.

Figure 1:
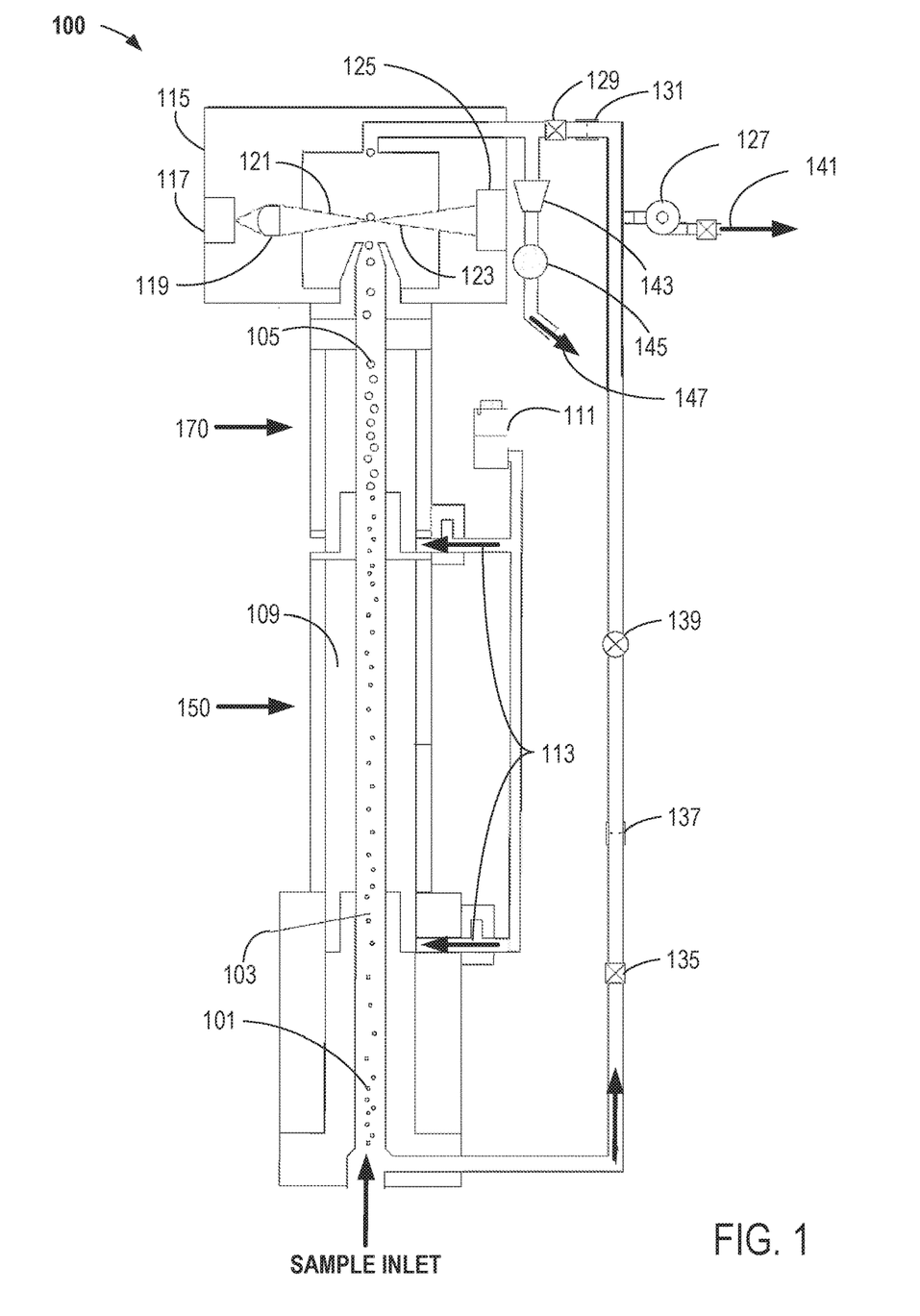
FIG. 1 shows a generalized cross-sectional view of a water-based condensation particle counted (CPC)

With reference now to FIG. 1, a generalized cross-sectional view of a water-based condensation particle counter (CPC) 100 is shown. The water-based CPC 100 is used to monitor a particle concentration level within a given environment (e.g., a semiconductor-fabrication facility). The thermodynamic considerations governing operations of water-based CPCs is known in the art and therefore will not be discussed in significant detail herein.

The water-based CPC 100 is shown to include a flow path 101 directing an aerosol sample flow 103 through a porous media 109. The porous media 109 is also referred to as a wick and may comprise one or more various types of hydrophilic material. The porous media 109 may comprise a continuous material from the sample inlet to at or near an optical particle detector 115 (described in more detail below). Alternatively, the porous media 109 may comprise different sections or portions along the path of the aerosol sample flow 103.

In this embodiment, the porous media 109 is supplied with liquid water from a water fill bottle 111 along two water-inlet paths 113. Depending on a specific design of the water-based CPC 100, the number of water-inlet paths 113 may decrease to a single inlet path or the number on inlet paths may increase. Such determinations for the actual number of water-inlet paths 113 may be determined by a person of ordinary skill in the art based on aerosol flow rates, thermodynamics of the system, and other considerations of the water-based CPC 100. The first (closest to the sample inlet) of the water-inlet paths 113 supplies water to the porous media 109 just before a cooled conditioner portion 150 of the water-based CPC 100. The second of the water-inlet paths 113, downstream of the first, supplies additional water just before a heated-growth portion 170 of the water-based CPC 100. As noted in FIG. 1, smaller particles from the sample inlet have "grown" in size due to condensation of water vapor onto the particles. Large particles have a different and generally larger scattering signature than small particles. Consequently, larger particles 105 with a condensation layer are now more readily detected by the optical particle detector 115 than the smaller particles entering the sample inlet.

For example, the larger particles 105 in the flow path comprising the aerosol stream cross a "focus point" of a beam of light 121 emitted by a light source 117, typically a solid-state laser diode. The focus point is formed by an optical element 119 focusing light (e.g., to a diffraction limited point or line that is generally perpendicular to both the direction of the light beam and the aerosol flow path) output from the light source 117. Scattered radiation 123 individually created by each of the larger particles 105 is sensed by an optical detector 125. The larger particles 105 continue out of the optical particle detector 115 and are either captured by a filter 129 or continue into a water separator 143. Either periodically or continuously, the water separator 143 is drained by a drain pump 145 to a water drain discharge 147.

Overall aerosol flow through the flow path 101 is maintained by a sample-flow pump 127. In the embodiment shown in FIG. 1, the aerosol flow rate is maintained by a critical orifice 131. In other embodiments, a standard orifice or other type of flow control mechanism may be employed. Critical orifices are frequently used in gas-flow sampling instruments as they are able to maintain a constant flow rate provided a sufficient differential pressure is maintained across the orifice. The sample-flow pump 127 may either be a pump internal to the water-based CPC 100 or may be an externally-connected pump. In some embodiments, the water-based CPC 100 may be connected directly to a vacuum-supply source plumbed within a facility (e.g., a vacuum-supply source of the semiconductor-fabrication facility). Pump exhaust 141 is filtered prior to release to ambient air so as not to increase a contamination level of the monitored environment.

The sample-flow pump 127 may also provide a flow from the sample inlet through a secondary gas-flow path that includes a transport flow filter 135, a second critical orifice 137 and an optional transport flow valve 139. The optional transport flow valve 139 may be used to reduce a total gas flow rate if the differential pressure across the second critical orifice is not sufficient to maintain a constant pressure.

Referring now to FIG. 2A, a cross-section of a water-based CPC 200 is shown and incorporates many of the false-particle count reduction embodiments disclosed herein. Additional details of the water-based CPC 200 are discussed with reference to FIG. 2B (indicated by section line A-A) and FIG. 2C (indicated by section line B-B), below. The water-based CPC 200 functions similarly in basic operation to the water-based CPC 100 of FIG. 1. Additionally, the water-based CPC 200 is shown to include a removable wick cartridge 201 that may be configured to be readily removable by the end-user. The removable wick cartridge 201 includes a wick stand 203 that is affixed over the removable wick cartridge 201 and a conical section 205. Adjacent to the removable wick cartridge 201 is a drain sidecar 207 having a drain reservoir 209 formed therein.

A sample inlet (shown and described in more detail with reference to FIG. 2B below) is located near a lower edge of the removable wick cartridge 201. Particles contained within an aerosol stream arriving through the sample inlet traverse a flow path 213 through one or more wicks 211. In the various views shown by FIGS. 2A through 4C, three wicks are used to form the flow paths 213. However, this number may be changed depending on factors related to maintaining a sufficiently low Reynolds number to maintain a laminar flow of the aerosol stream through the one or more flow paths 213. Such factors are known to a skilled artisan and include determining a ratio of inertial forces to viscous forces of the aerosol flow based on a mean velocity and density of the fluid in the aerosol stream, as well as dynamic and kinematic viscosities of the fluid, and a characteristic linear dimension relating to an internal cross-section of the wicks. Additionally, a single wick with multiple paths formed therein (e.g., by drilling out the paths) may also be used.

The wick stand 203 splits the incoming aerosol stream and contains a number of outlet paths equal to the number of wicks. In the embodiment, depicted by FIG. 2A, the wick stand 203 has three outlet paths. As described in more detail with reference to FIG. 4A through FIG. 4C, the wick stand also provides a physical mechanical-interface onto which the wicks 211 are mounted. When more than one wick is used, a flow joiner 215 combines particles from the three aerosol streams into a single aerosol stream immediately prior to a particle detection chamber 219. The particle detection chamber may be similar to the optical particle detector 115 of FIG. 1.

Figure 2A:
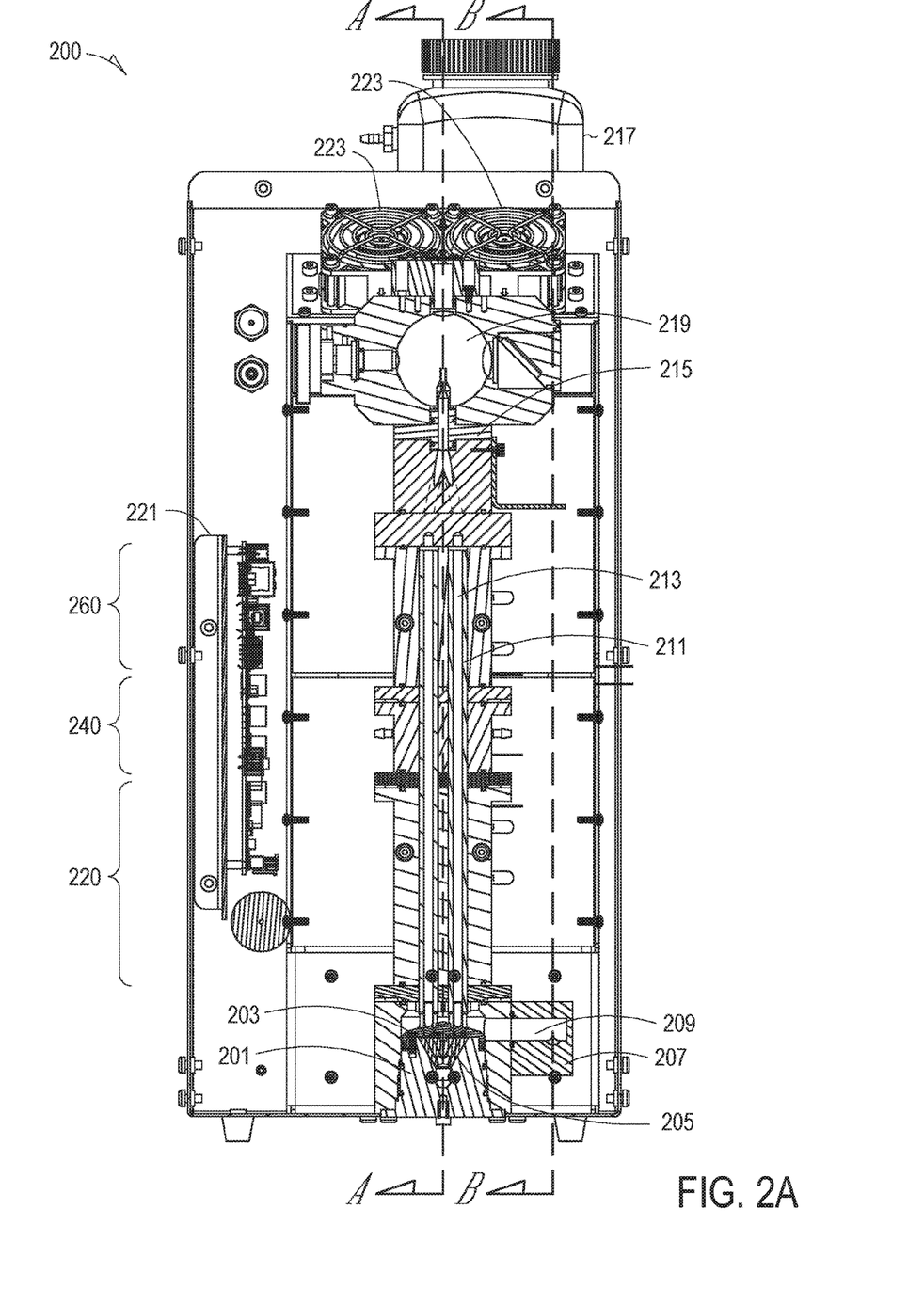
FIG. 2A shows a cross-section of a water-based CPC that incorporates many of the false-particle count reduction embodiments disclosed herein.

One or more cooling fans 223 reduce or eliminate any excess heat produced within the water-based CPC 200 by, for example, one or more circuit boards 221, as well as heating elements and thermo-electric devices, as discussed in more detail below.

Similar to the basic thermodynamic principles discussed with reference to the CPC of FIG. 1, the water-based CPC 200 of FIG. 2A shows a conditioner portion 220, an initiator portion 240, and a moderator portion 260. The conditioner portion 220 is cooled to begin the process of forming a condensate on particles in the aerosol stream. The initiator portion 240 is heated and is the portion of the water-based CPC 200 where condensate is formed on each of the individual particles. The moderator portion 260 is cooled sufficiently, relative to the initiator portion 240, such that moist air entering the particle detection chamber 219 is reduced or eliminated. A water fill bottle 217 provides a reservoir of clean water (e.g., NPLC, other ultra-pure water, or distilled water) to keep the wicks 211 hydrated to provide water vapor in the flow path 213 to condense on the particles. However, either an excess volume of water, or water provided to the wicks 211 too rapidly (e.g., when supplied in "spurts"), can contribute to the formation of either water bubbles or empty droplets not containing any particles. Either of these conditions can lead to an increase in false-particle counts.

In one embodiment, water from the water fill bottle 217 is supplied to the wicks 211 by gravity feed. In another embodiment, water from the water fill bottle 217 is supplied to the wicks 211 periodically through water pumps (described with reference to FIG. 2B, below). In another embodiment, water from the water fill bottle 217 is supplied to the wicks 211 either continuously or periodically through a syringe-injection arrangement (not shown specifically but understood by a skilled artisan). In another embodiment, the water fill bottle may be either slightly pressurized or driven with a pneumatic or hydraulic ram system to act as a type of syringe-injection system. In another embodiment, water from the water fill bottle 217 is supplied to the wicks 211 periodically from either the water pumps or one of the types of syringe-injection system through a pulsation damper (e.g., a reservoir designed to reduce or eliminate rapid increase in volumetric flow of the water). By supplying the water either continuously (e.g., through syringe-injection) or periodically (e.g., utilizing the pulsation damper mechanism), excess water over a short period of time to the wicks is reduced or eliminated. In various embodiments, hydrogen peroxide may be added to the water fill bottle 217 to prevent bacterial growth. In various embodiments, silver impregnation of the wicks or other bio-inhibitors may be employed either separately from or in combination with hydrogen peroxide added to the water fill bottle. Like particles in the aerosol stream, bacteria formed within the water can be the basis of a nucleation point in the flow path 213. Condensed water on the bacteria flowing into the particle detection chamber 219 will then be counted as a particle. The bacteria therefore can also increase the false-particle count of the CPC.

Figure 2B:
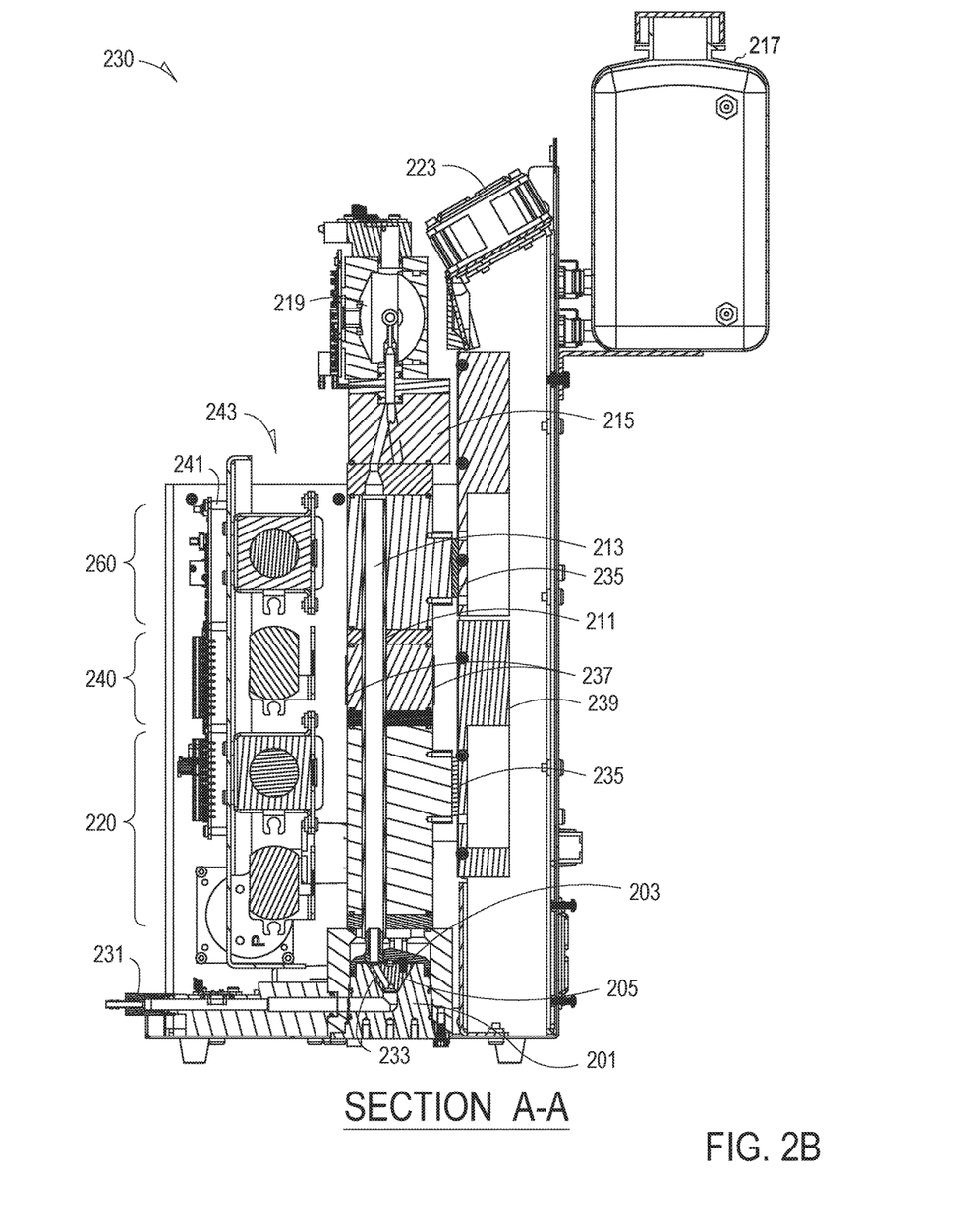
FIG. 2B shows a cross-section of the water-based CPC of FIG. 2A along section A-A.

Referring now to FIG. 2B, a cross-section 230 of the water-based CPC 200 along section A-A of FIG. 2A is shown. The cross-section 230 more clearly indicates both the sample inlet 231 and a flow-splitter arrangement 233 as discussed with reference to FIG. 2A above. The cross-section 230 is also shown to include thereto-electric devices 235 thermally coupled to each of the conditioner portion 220 and the moderator portion 260, heating elements 237 thermally coupled to the initiator portion 240, and a heat sink 239 in thermal communication with the cooling fans 223. Also shown are a secondary circuit board 241 and a number of water pumps 243.

With continuing reference to FIG. 2B, the conical section 205 of the removable wick cartridge 201 is in thermal contact with the flow-splitter arrangement. In various embodiments, the conical section 205 may be heated to compensate for differences in the relative humidity of a monitored environment. Although not shown specifically, the ambient temperature and the dew-point temperature may be determined by appropriate temperature-measurement devices. Alternatively or in addition, a humidity sensor may be used to determine relative humidity of the monitored environment. In various other embodiments, both inlet and outlet dew points may be monitored. In all cases, heating the conical section 205 may reduce or eliminate effects from varying levels of relative humidity that cause bubbles or empty water droplets to form due to elevated levels of relative humidity.

Figure 2C:
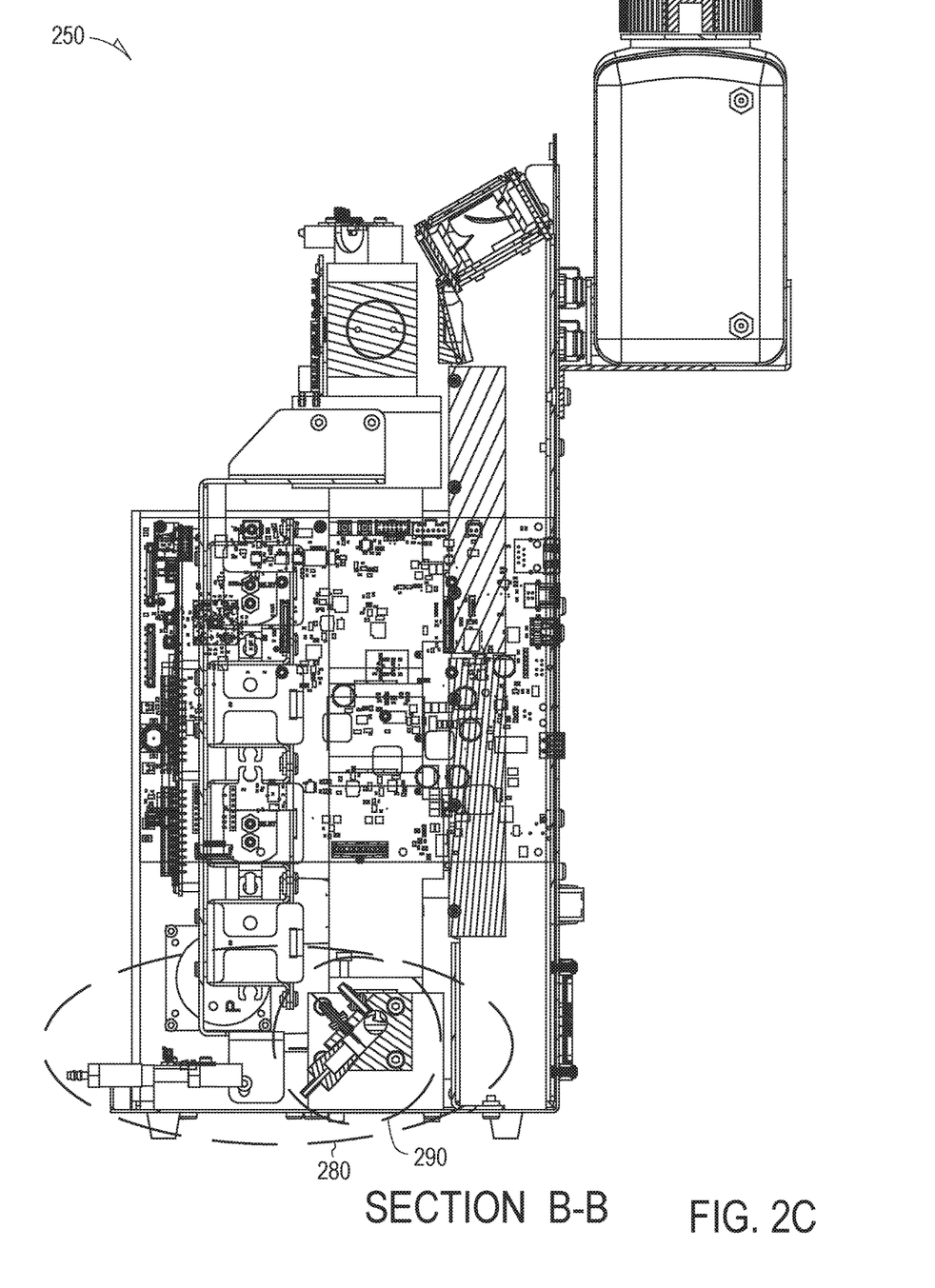
FIG. 2C shows a cross-section of the water-based CPC of FIG. 2A along section B-B.

With reference to FIG. 2C, a cross-section 250 of the water-based CPC 200 along section B-B of FIG. 2A is shown. The cross-section 250 shows an exemplary location of a combination sample inlet/wick cartridge portion 280 and a detailed view 290 of the drain sidecar 207 portion. However, the portions may be located in other areas with regard to the water-based CPC 200. The exemplary location shown is merely provided for ease of understanding the disclosed subject matter. Each of the combination sample inlet/wick cartridge portion 280 and the detailed view 290 of the drain sidecar 207 portion was discussed briefly above with reference to FIG. 2A.

Figure 3A:
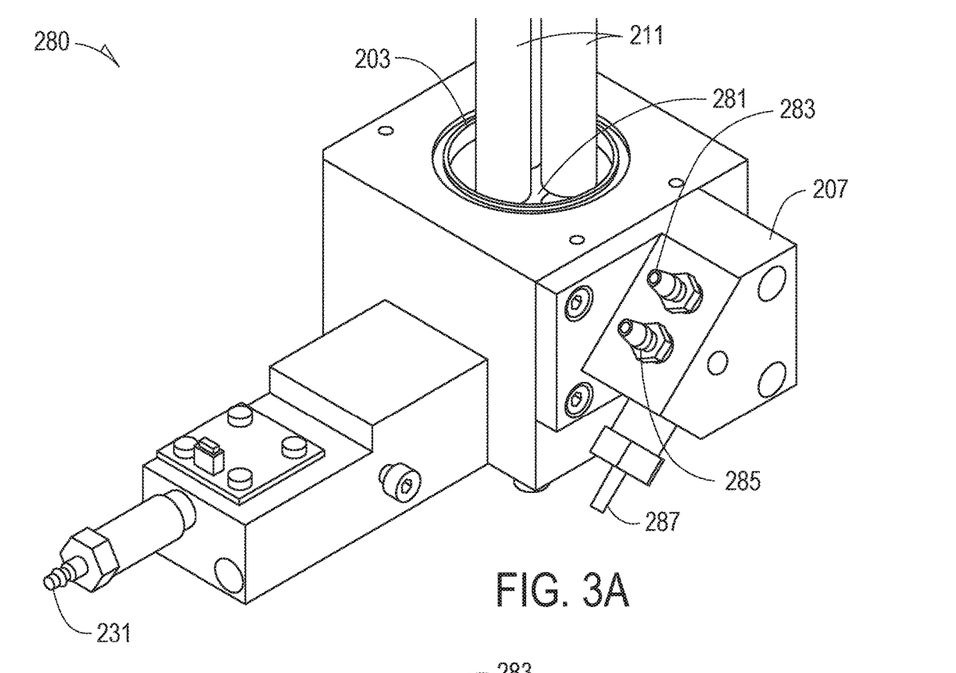
FIG. 3A shows an isometric view of an embodiment of a combination sample inlet/wick cartridge portion and a drain sidecar portion of FIG. 2C.
Figure 3B:
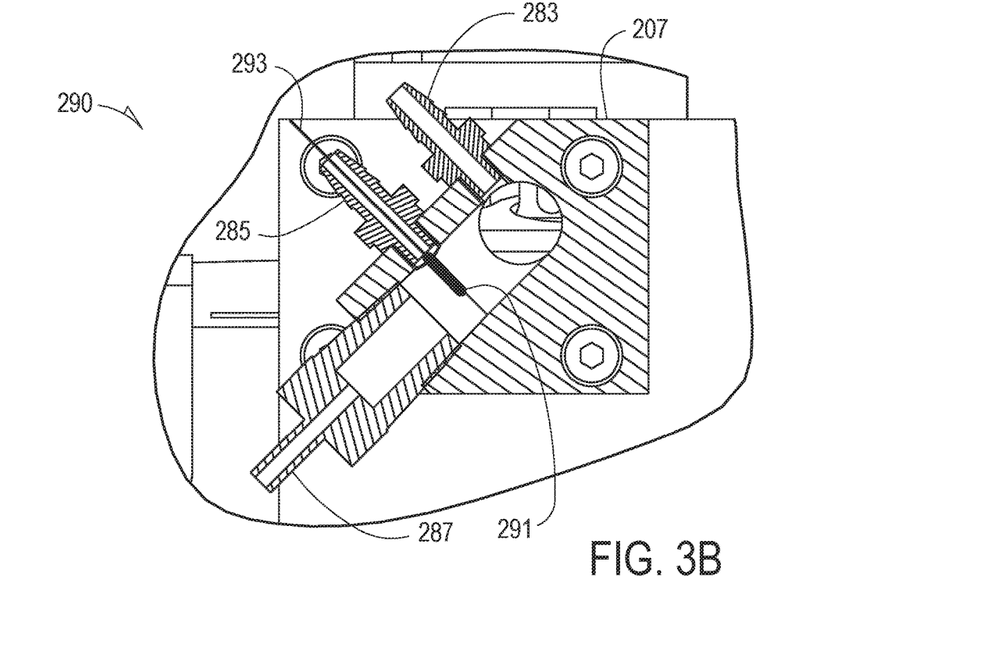
FIG. 3B shows a detailed view of the drain sidecar portion of the embodiment of FIGS. 2C and 3A.

FIG. 3A shows an isometric view of the combination sample inlet/wick cartridge portion 280 and FIG. 3B shows the detailed view 290 of the drain sidecar 207 portion. As shown, the wicks 211 are mounted vertically in the wick stand 203 and are surrounded by a water reservoir 281. Although generally, the water reservoir collects excess water from the wicks 211, in various embodiments, the wicks 211 may be supplied with water from the water reservoir 281 or may be supplied by water-inlet paths 113 as shown in FIG. 1. In other embodiments, a combination of both the water reservoir 281 and the water-inlet paths 113 may supply water to the wicks 211. In still other embodiments, the water-inlet path 113 may only supply water to the wicks 211 at the initiator portion 240, or the moderator portion 260, but not both. This latter embodiment may be coupled with a supply of water to the wicks at the water reservoir 281. In still other embodiments, water may only be supplied to the wicks 211 at either the initiator portion 240, or the moderator portion 260, but not to the water reservoir 281. In this embodiment, the water reservoir 281 serves to capture excess water to be delivered to the drain sidecar 207. Generally, regardless of the water delivery technique chosen, air bubbles in delivery lines to the wicks 211 should be avoided to reduce or eliminate water bubbles being formed within the flow path 213 (see FIGS. 2A and 2B). Also, any dead air volumes within the water delivery paths are avoided.

However, regardless of how the water is supplied to the wicks 211, any excess water should be drained off before it causes bubbles or empty water droplets in the aerosol stream flowing through the flow path 213 (see FIG. 2A and FIG. 2B). The drain sidecar 207, discussed briefly above with reference to FIG. 2A, is shown to include an exhaust-air port 283, a water-sensor port 285, and a water-drain port 287. The exhaust-air port 283 allows water from the water reservoir 281 to drain more readily by drawing air and may be coupled to, for example, the sample-flow pump 127 (FIG. 1) or another pump mounted either internal to or external to the water-based CPC 200.

Referring now to FIG. 3B, a detailed view 290 of the drain sidecar 207 portion is shown including the water-sensor port 285 includes a water sensor 291. When water is supplied to the wicks 211, excess water from the wicks 211 drains into the water reservoir 281. When the water supply to the wicks 211 is sufficient, the water sensor 291 then supplies a signal to stop the water supply. The water sensor 291 may be electrically coupled via an electrical lead to one of the circuit boards 221, 241 (FIGS. 2A and 2B, respectively) to determine when water is present in the drain sidecar 207. A constant air flow through the exhaust-air port 283 pulls water from the water reservoir 281 toward the drain sidecar 207. The drain sidecar 207 includes the water sensor 291 that detects when the drain fills with water to a certain predetermined level, at which point the water is extracted by a separate pump (not shown in FIG. 3B).

In other embodiments, the water sensor may instead comprise a temperature sensing device (e.g., a thermocouple or thermistor) or a humidity sensing device to determine when water is present in the drain sidecar 207. Once water is detected, the water is pumped out of the drain sidecar 207 through the water-drain port 287 by, for example, a solenoid-activated micro-pump. In a specific exemplary embodiment, the micro-pump may draw water at a variable approximate flow rate of from about 50μ-liters/minute to about 200μ-liters/minute. In other embodiments, the micro-pump may draw water at a substantially constant approximate flow rate of about 150μ-liters/minute.

Figure 4A:
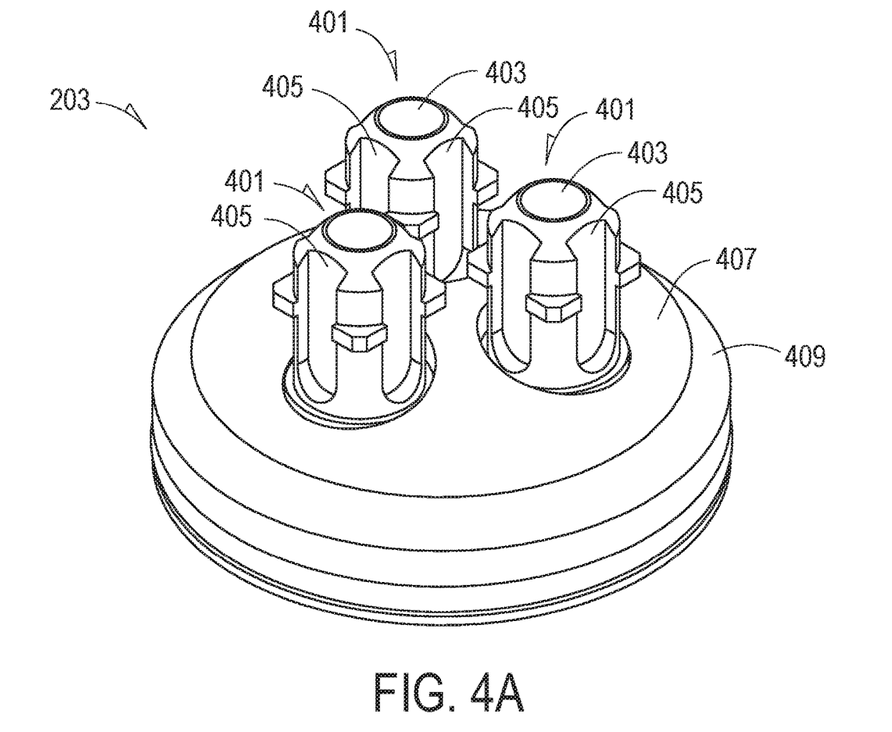
FIG. 4A through 4C show various views of an exemplary embodiment of a wick stand of FIGS. 2A and 2B.

FIG. 4A shows an isometric top view of the wick stand 203 described briefly above with reference to FIGS. 2A and 2B. The wick stand 203 is shown to provide three mechanical mounts 401, one for each of the three wicks 211. As stated above, other numbers of wicks 211, and consequently, the number of related mechanical mounts 401, may be chosen. Each of the three mechanical mounts 401 includes an opening 403 through which the aerosol stream may pass, and a number of grooves 405 through which excess amounts of water in the wicks 211 may pass to the water reservoir (FIG. 3A).

Figure 4B:
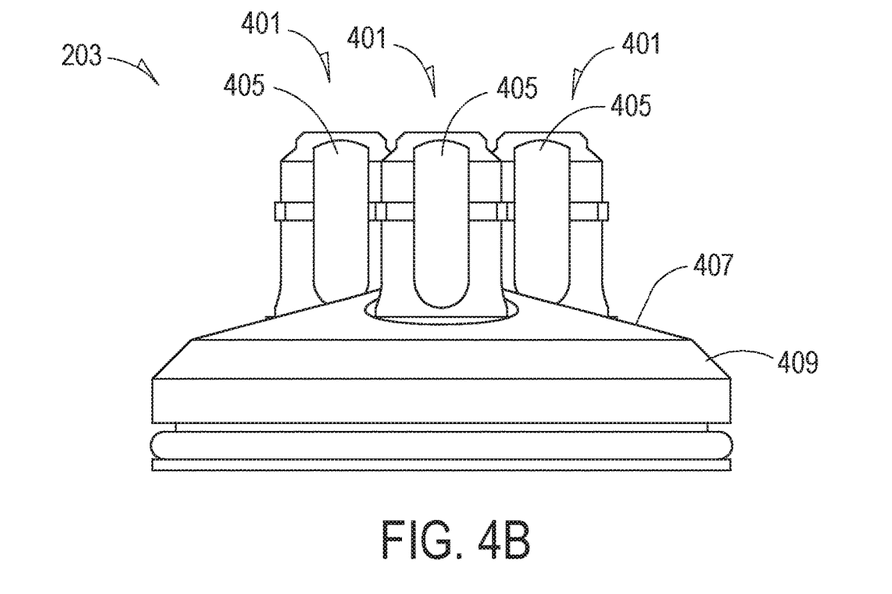

In FIG. 4B, which shows a side elevational-view of the wick stand 203, the excess water channeled through the grooves 405 drains from a first sloped surface 407 to a second sloped surface 409 to the water reservoir 281 of FIG. 3A. In various embodiments, only a single sloped surface may be employed. Also, the sloped surface may comprise a curved top surface rather than a single flat surface. In a specific exemplary embodiment, the first sloped surface 407 has an angle of about 15 degrees as measured from a horizontal plane and the second sloped surface 409 has an angle of about 45 degrees as measured from the horizontal plane.

Figure 4C:
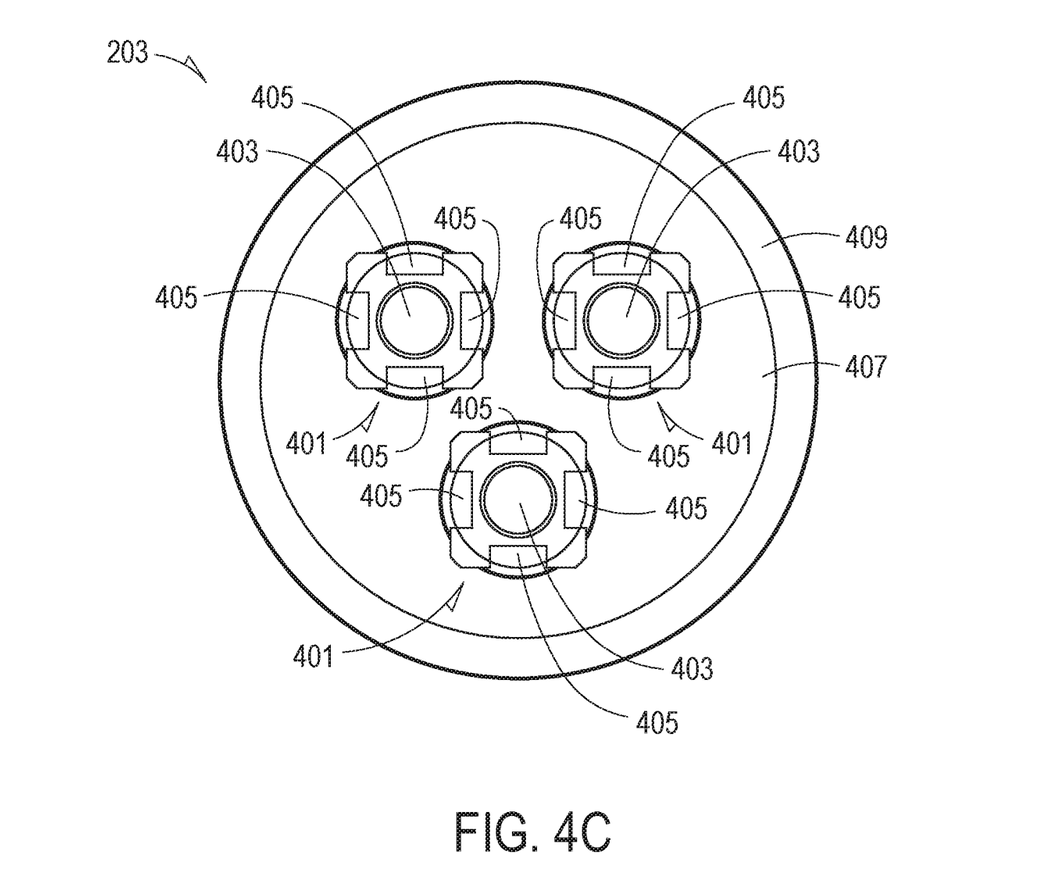

FIG. 4C shows a top view of the wick stand 203. Although each of the three mechanical mounts 401 is shown to include four grooves, a skilled artisan will recognize that more or fewer grooves may be employed. Also, a size of the grooves is at least partially dependent on a size of the opening 403 and an external diameter of the mechanical mount 401 (the external diameter being sized to accommodate an inner diameter of a selected wick).

In various embodiments, any or all of the false-particle count reduction techniques discussed may be coupled with a digital filtering technique. Digital filtering, in the context of CPC false-particle count reduction, is based on one or more observed phenomenon that distinguishes water bubbles or water droplets from actual particles having condensed water famed thereon. For example, a pulse height analyzer or an oscilloscope may be electrically coupled to a detector in the particle detection chamber 219. The rise time and/or the shape of a resultant pulse can be used to characterize and differentiate an actual particle from a bubble or empty droplet. In one embodiment, an "absolute filter" (e.g., a HEPA or ULPA filter) may be placed over the sample inlet 231 so that any signal generated by the detector is a known-false particle count and the resultant signal is therefore analyzed and characterized. These signals may be stored in a look-up table. In a subsequent actual use of the CPC in a monitored environment, each of the generated signals is compared with the saved signals in the look-up table. Any signals matching the characteristics of the resultant signals of the known-false particles are automatically subtracted out of the final reported particle count.

Although specific values, ranges of values, and techniques are given various parameters discussed above, these values and techniques are provided merely to aid the person of ordinary skill in the art in understanding certain characteristics of the designs disclosed herein. Those of ordinary skill in the art will realize, upon reading and understanding the disclosure provided herein, that these values and techniques are presented as examples only and numerous other values, ranges of values, and techniques may be employed while still benefiting from the novel designs discussed herein that may be employed to lower false-counts in water-based CPCs. Therefore, the various illustrations of the apparatus are intended to provide a general understanding of the structure and design of various embodiments and are not intended to provide a complete description of all the elements and features of the apparatus that might make use of the structures, features, and designs described herein.

Many modifications and variations can be made, as will be apparent to a person of ordinary skill in the art upon reading and understanding the disclosure provided herein. Functionally equivalent methods and devices within the scope of the disclosure, in addition to those enumerated herein, will be apparent to a person of ordinary skill in the art from the foregoing descriptions. Portions and features of some embodiments may be included in, or substituted for, those of others. Many other embodiments will be apparent to those of ordinary skill in the art upon reading and understanding the description provided herein. Such modifications and variations are intended to fall within a scope of the appended claims. The present disclosure is to be limited only by the terms of the appended claims, along with the full scope of equivalents to which such claims are entitled. It is also to be understood that the terminology used herein is for the purpose of describing particular embodiments only and is not intended to be limiting.

The Abstract of the Disclosure is provided to allow the reader to quickly ascertain the nature of the technical disclosure. The abstract is submitted with the understanding that it will not be used to interpret or limit the claims. In addition, in the foregoing Detailed Description, it may be seen that various features may be grouped together in a single embodiment for the purpose of streamlining the disclosure. This method of disclosure is not to be interpreted as limiting the claims. Thus, the following claims are hereby incorporated into the Detailed Description, with each claim standing on its own as a separate embodiment.

What is claimed is:

1. A method of reducing false-particle counts in a water-based condensation particle counter (CPC), the method comprising:
    delivering water into a plurality of wicks, each of the plurality of wicks being formed from a porous media material with an open portion formed therethrough along a length of the wick, the open portion forming an inner diameter of respective ones of the plurality of wicks for directing a separate aerosol sample flow within respective ones of each of the plurality of wicks, the plurality of wicks being substantially parallel and adjacent to one another within the water-based CPC and extending from a wick stand on a first end of the plurality of wicks to a flow joiner on a second end of the plurality of wicks, the flow joiner for combining particles from the aerosol sample flows from the plurality of wicks into a single aerosol stream immediately prior to a particle detection chamber within the CPC, each of the plurality of wicks for transporting separate portions of the delivered water;
    sensing an excess volume of water delivered to the plurality of wicks;
    collecting the excess volume of water into a collection reservoir; and
    draining the excess volume of water from the collection reservoir.

2. The method of claim 1, further comprising pulling a constant air flow through an exhaust-air port to drain the excess volume of water.

3. The method of claim 1, further comprising detecting when a drain is filled with water to a predetermined level.

4. The method of claim 1, further comprising draining the excess water volume by pumping the excess water volume.

5. The method of claim 1, further comprising applying a digital filter to further reduce false-particle counts.

6. The method of claim 1, further comprising comparing detected particle counts with a look-up table to subtract false-particle counts.

7. The method of claim 6, further comprising constructing the look-up table by storing signatures of detected signals produced by known false-particles.

8. A system to reduce false-particle counts in a water-based condensation particle counter (CPC), the system comprising:
    an aerosol sample inlet configured to be coupled to a sample flow pump;
    a plurality of wicks to receive water, each of the plurality of wicks being formed from a porous media material with an open portion formed therethrough along a length of the wick, the open portion forming an inner diameter of respective ones of the plurality of wicks and being configured to direct a separate aerosol sample flow within each of the plurality of wicks, the plurality of wicks being substantially parallel and adjacent to one another within the water-based CPC from a wick stand coupled to the aerosol sample inlet on a first end of the plurality of wicks to a flow joiner coupled to the sample flow pump on a second end of the plurality of wicks, the flow joiner configured to combine particles from the aerosol sample flow within each of the plurality of wicks into a single aerosol stream immediately prior to a particle detection chamber within the CPC, each of the plurality of wicks being configured to transport separate portions of the received water;
    a collection reservoir to collect an excess volume of water from the plurality of wicks; and
    a sensor to provide a signal corresponding to the excess volume of water in the plurality of wicks.

9. The system of claim 8, further comprising a water drain port coupled to the collection reservoir to remove excess water.

10. The system of claim 8, wherein the plurality of wicks is field replaceable by an end-user of the CPC.

11. The system of claim 8, wherein the sensor is to detect when the collection reservoir is filled with water to a predetermined level.

12. The system of claim 8, further comprising a digital filter to further reduce the false-particle counts.

13. The system of claim 12, wherein the digital filter is to compare detected particle counts with a look-up table to subtract false-particle counts.

14. The system of claim 13, wherein the look-up table includes a plurality of stored signatures of detected signals produced by known false-particles.

15. The system of claim 8, wherein the plurality of wicks is silver impregnated to reduce or prevent bacterial growth within the plurality of wicks.

16. The system of claim 8, wherein the plurality of wicks is treated with a bio-inhibitor to reduce or prevent bacterial growth within the plurality of wicks.

17. The system of claim 8, further comprising a removable wick cartridge coupled to the wick stand onto which the plurality of wicks is mounted, the removable wick cartridge configured to be heated to reduce or eliminate effects from varying levels of relative humidity, thereby reducing or eliminating bubbles or empty water droplets due to elevated levels of relative humidity.

18. A system to reduce false-particle counts in a water-based condensation particle counter (CPC), the system comprising:
    an aerosol sample inlet configured to be coupled to a sample flow pump;

a single wick to receive water, the single wick being a porous media having multiple separate aerosol flow paths formed therethrough along a length of the single wick, each of the multiple separate aerosol flow paths being surrounded along a length of the path by the porous media with each comprising an open portion being configured to direct an aerosol sample flow therein, each of the multiple separate aerosol flow paths being substantially parallel and adjacent to one another within the water-based CPC from a wick stand coupled to the aerosol sample inlet on a first end of the single wick to a flow joiner coupled to the sample flow pump on a second end of the single wick, the flow joiner configured to combine particles from the multiple separate aerosol flow paths into a single aerosol stream immediately prior to a particle detection chamber within the CPC, the single wick being configured to transport separate portions of the received water; and a collection reservoir to collect the excess volume of water from the single wick.

19. The system of claim 18, further comprising a sensor to make a determination whether an excess volume of water is delivered to the single wick.

20. The system of claim 19, wherein the sensor includes one or more sensors selected from various types of sensors including a water sensor, a temperature sensing device, and a humidity sensing device, the sensor being configured to generate a signal to stop a supply of water sent to the single wick.

* * * * *